United States Patent [19]

Gibs

[11] Patent Number: 4,675,293

[45] Date of Patent: Jun. 23, 1987

[54] PREPARATION OF MALTOSE AND MALTITOL SYRUPS

[75] Inventor: Gabriel J. Gibs, Pearl River, N.Y.

[73] Assignee: Lonza Inc., Fair Lawn, N.J.

[21] Appl. No.: 640,890

[22] Filed: Aug. 15, 1984

[51] Int. Cl.[4] ........................ C12P 19/22; C12P 19/20; C12P 19/16

[52] U.S. Cl. ........................................ 435/95; 435/96; 435/98; 536/1.1

[58] Field of Search ............................... 435/95, 98, 99

[56] References Cited

U.S. PATENT DOCUMENTS

| | | | |
|---|---|---|---|
| 3,804,715 | 4/1974 | Sugimoto et al. | 435/95 |
| 3,998,696 | 12/1976 | Yomoto et al. | 435/98 |
| 4,346,116 | 8/1982 | Verwaerde et al. | 435/98 X |

*Primary Examiner*—Lionel M. Shapiro
*Attorney, Agent, or Firm*—Bert J. Lewen; Henry Sternberg

[57] ABSTRACT

The invention relates to the preparation of a high maltose syrup containing from 60 to 80% maltose, from 12 to 24% glucose and from 8 to 16% sugars having a DP of three or more by the enzymatic saccharification of partially hydrolyzed starch having a dextrose equivalence of from 1 to about 30; the high maltose syrups obtained from such process; the hydrogenation of such high maltose syrup to form maltitol blends containing from 60 to 80% maltitol and from 12 to 24% sorbitol; and the so prepared maltitol blends, such blends having a desired combination of high sweetness and humectancy.

4 Claims, No Drawings

PREPARATION OF MALTOSE AND MALTITOL SYRUPS

BACKGROUND OF THE INVENTION

It has long been desired to produce bulk sweeteners exhibiting a combination of properties including sweetness, high humectancy (hygroscopicity), non-cariogenicity, crystallization inhibition and potential use for diabetics. Such sweeteners are useful in the manufacture of non-cariogenic and diabetic foods and confections, baked goods, animal foods, oral hygiene products and pharmaceuticals.

Although there are bulk sweeteners which meet some of the above requirements, none of them have all the desired characteristics and all have certain deficiencies. Sucrose, fructose and other sugars, although they have intense sweetness, are cariogenic and have only low humectancy.

One type of sweetener which meets many of the above requirements is conventional maltitol syrups. Some of these contain over 60% maltitol and are prepared by the hydrogenation of conventional high maltose syrups having over 60% maltose and only a minimum of glucose, generally less than 10% and most commonly less than 5%. However, thus prepared maltitol syrups are low in sorbitol, a component which has both high humectancy and sweetness. In order to improve the humectancy and sweetness of these products, they may require further compounding with addition of sorbitol. The maltitol compositions claimed herein are improvements over prior, conventional maltitol syrups since they inherently provide desired combinations of sweetness and humectancy, thus eliminating the need of additional compounding with sorbitol.

The preparation of conventional high maltose syrups is described in the prior art. For example, U.S. Pat. Nos. 3,795,584 and 3,804,715 assigned to Hayashibara show the saccharification of liquified starch to produce high maltose solutions using beta-amylase and alpha-1,6-glucosidase (pullulanase). However, such sugar compositions contain a maximum of a few percent of glucose.

CPC International U.S. Pat. No. 3,565,765 also teaches the formation of high maltose syrups using a combination of enzymes. This patent teaches the simultaneous use of a maltogenic enzyme and pullulanase to form high maltose syrups. While higher glucose levels than the Hayashibara patents are reported, the maximum amounts shown are less than 10%, generally less than 5%, and the sugars having a degree of polymerization of three or more are most frequently over 10%.

Another patent showing the enzymatic conversion is the A. E. Staley U.S. Pat. No. 3,791,865. It teaches the use of a mixture of beta-amylase and amylo-1,6-glucosidase to form high maltose syrups having small, even trace, amounts of glucose and having maltotriose contents of greater than 18%. CPC International's U.S. Pat. No. 3,549,496 shows the conversion of partially hydrolyzed starch into compositions containing maltose and up to 45% of glucose using Bacillus polymyxa amylase in a first conversion followed by glucoamylase. Such products have comparatively low maltose concentrations and high concentrations of saccharides having a degree of polymerization of three or more.

Other patents which show the production of high maltose compositions include Hayashibara U.S. Pat. Nos. 3,832,285 and 4,032,403; AB Stadex U.S. Pat. No. 3,996,107; Meiji Seika Kaisha U.S. Pat. No. 3,998,696; and CPC International U.S. Pat. No. 4,113,509.

BRIEF DESCRIPTION OF THE INVENTION

The invention relates to a method of preparing such high maltose syrups by the enzymatic saccharification of partially hydrolyzed starch having a dextrose equivalence (DE) from 1 to 30, preferably from 5 to 30, in the presence of three enzymes, namely, beta-amylase; alpha-1,6-glucosidase; and fungal alpha-amylase; and the two-step process for preparing high maltitol syrups comprising the aforesaid saccharification step and the hydrogenation of the products thereof. In addition, the invention relates to a high maltose syrup containing from 60 to 80% maltose, from 12 to 24% glucose and from 8 to 16% saccharides having a degree of polymerization (DP) of three or more, such as may be produced by the process of the invention.

A further embodiment of this invention is the product obtained from the hydrogenation of the aforementioned high maltose blend. These hydrogenation products contain from 60 to 80% maltitol, from 12 to 24% sorbitol, and from 8 to 16% maltotriitol and other hydrogenated products having a DP of three or more.

The latter compounds are particularly useful for the preparation of products where high sweetness and humectancy are desired. Examples of such applications are: chewing gums, non-cariogenic confections, jams and jellies, baked goods, animal foods, toothpaste, and a great variety of diabetic and dietetic foods.

DETAILED DESCRIPTION OF THE INVENTION

The high maltose product of this invention is prepared from a partially hydrolyzed starch having a dextrose equivalence from 1 to 30, preferably from about 5 to 30. The formation of such partially hydrolyzed starches is well known and they may be commercially prepared by heating the starch with hydrochloric or sulfuric acid at a high temperature and then neutralizing the hydrolysis mixture with sodium carbonate, or, alternatively, by an enzymatic process, also performed at a high temperature, using alpha-amylase as the enzyme. This enzyme effectively hydrolyzes the starch by cleaving one molecule of glucose at a time from the starch molecule. These "thinning steps" are described in the abovementioned U.S. Pat. No. 4,113,509.

Examples of "partially hydrolyzed starch" which may be used in the preparation of the high maltose syrup of the invention include maltodextrin and waxy maize syrup having a DE of 4 to 20, liquid starch having a DE of 1 to 2, and low conversion corn syrup having a DE of 20 to 30. Such products are well known to those skilled in the art.

In the process of this invention, the partially hydrolyzed starch is further saccharified in the presence of three enzymes, namely, beta-amylase, alpha-1,6-glucosidase (as, for example, pullulanase), and fungal alpha-amylase. The first two of these materials are readily available from EDC Corporation, BIOCON, and Fermco Biochemics Inc., and the third, known commercially as Fungamyl 800L, from Novo Corporation. The reaction may be readily carried out by employing about equal quantities of the beta-amylase and the alpha-1,6-glucosidase and at least 10% of the fungal alpha-amylase. Generally speaking, from 30 to 50% of each of the first two enzymes is used and from 10 to 40% of the third.

The reaction is best carried out in an aqueous medium containing less than 45% solids, most preferably from 25 to 35%, while the pH of the solution is maintained in the range of 4.5 to 6, preferably from 5.0 to 5.5. The reaction temperature is generally from 40° to 60° C., preferably from 45° to 55° C., and the reaction time from 36 to 144 hours. Based on solids, the total enzymes used are at least 0.1%, but not more than 1%; preferably from 0.3 to 0.5% of total enzymes are used.

By following the aforementioned process of the invention, a high maltose syrup is obtained containing from 60 to 80% maltose, from 12 to 24% glucose, and from 8 to 16% saccharides having a DP of three or more. Such products are useful in candy compositions, dessert formulations, and, because of their high fermentable contents, for the baking and brewing industries. In addition, such compounds may be readily hydrogenated to form high sorbitol-maltitol mixtures by following well-known hydrogenation techniques. The hydrogenation of the high maltose syrups of the invention may be performed in the presence of Raney nickel or noble metal catalysts by contacting the high maltose syrups under pressure with hydrogen. The pH is generally maintained at from about 4.5 to less than 7. The following patents show the conventional technique for hydrogenation, the subject matter of which is incorporated by reference herein: U.S. Pat. No. 3,705,039, Hayashibara; U.S. Pat. No. 4,279,931, Roquette Freres; and U.S. Pat. No. 3,708,396, Hayashibara.

The products of the hydrogenation have a ratio of hydrogenated products which correspond substantially to the saccharides from which they are derived. It is common, however, depending on the conditions of the hydrogenation, for there to be some variation in the content of the corresponding hydrogenated products. Such alterations will be readily understood by those skilled in the art. Accordingly, the sorbitol/maltitol composition of the invention contains from 12 to 24% sorbitol, from 60 to 80% maltitol, and from 8 to 16% hydrogenated products having a DP of three or more. Such products are useful as sweeteners because of the high concentration of sorbitol in combination with the maltitol. Additionally, these latter products have greater humectancy than the prior art high maltitol compounds. This is particularly useful in the following applications: diabetic and dietetic foods, animal foods, candies, non-cariogenic chewing gum, toothpastes and mouthwashes.

In order to more clearly illustrate this invention, attention is directed to the following examples.

EXAMPLE 1

A waxy maize syrup (Maltodex 3260, trademark of A. E. Staley) containing 70% solids was diluted to 35% solids by adding 150 g of water to 150 g of the waxy maize syrup. The waxy maize syrup had a DE of 20. The solution was brought to a pH of 5.4 by the addition of a drop of 50% NaOH. The solution was placed in a 500 ml Erlenmeyer flask and 0.16 g of alpha-1,6-glucosidase (pullulanase), 0.16 g of beta-amylase, and 0.16 g of Fungamyl-L (trademark of Novo Corporation for alpha-fungal amylase) were added. The flask was thereafter capped and placed in a shaker water bath maintained at a temperature of 50° C. The flask was shaken at this temperature for 64 hours. The solution was then filtered to remove residual enzymes and analyzed by H.P. liquid chromatography to determine carbohydrate distribution. The analysis showed that the solution contained 14.3% glucose, 70.9% maltose, and 14.8% saccharides having a DP of three or more.

EXAMPLE 2

A low conversion corn syrup having a DE of 26 (Staley 200) was diluted to 35% solids. To 300 g of this diluted syrup in a 500 ml Erlenmayer flask were added 0.21 g of beta-amylase, 0.21 g of alpha-1,6-glucosidase and 0.09 g of Fungamyl L enzymes. The solution had a pH of 5.1. The flask was thereafter capped and placed in a shaker water bath maintained at a temperature of 45° C. After reacting for 89 hours, the product contained 17.8% glucose, 71.8% maltose and 10.5% saccharides having a DP of three or more.

EXAMPLE 3

This example shows the preparation of the sorbitol/maltitol composition of the invention. A high maltose syrup obtained by the procedure described in Example 2 but reacted only for 64 hours has the composition of 16% glucose, 70% maltose and 14% of saccharides having a DP of three or more. This syrup is hydrogenated using conventional techniques at 1000 psi of hydrogen at 135° C. in the presence of a Raney nickel catalyst for 5.5 hours.

The hydrogenation product is analyzed and found to contain 21% sorbitol, 64% maltitol and 15% hydrogenated compounds having a DP of three or more. Such product is ideally suitable as a humectant and/or sweetener in diabetic and dietetic foods, animal foods, non-cariogenic foods and confections, toothpastes and mouthwashes.

We claim:

1. A process for the saccharification of a partially hydrolyzed starch having a DE of from 1 to 30, comprises contacting such partially hydrolyzed starch under saccharification conditions with from 0.1 to 1 wt. % of a three-component enzyme composition, said three-component enzyme composition containing from about 30 to 50 wt. % each of beta-amylase and alpha-1,6-glucosidase and from 10 to 40 wt. % of fungal alpha-amylase, so as to form a polysaccharide composition containing from 60 to 80 wt. % maltose, from 12 to 24 wt. % glucose, and from 8 to 16 wt. % saccharides having a DP of 3 or more.

2. The process of claim 1, wherein the partially hydrolyzed starch is a maltodextrin, a waxy maize syrup, or a low conversion corn syrup.

3. The process of claim 1, wherein the saccharification takes place in an aqueous solution containing less than 45% of solids at a pH of from 4.5 to 6, at a temperature of from 45° to 60° C., and a reaction time of from 36 to 144 hours.

4. A process for the preparation of a high maltitol syrup which comprises: saccharifying a partially hydrolyzed starch having a DE of from 1 to 30 in the presence of from 0.1 to 1 wt. % of a three-component enzyme composition, said three-component enzyme composition comprising from about 30 to 50 wt. % each of beta-amylase and alpha-1,6-glucosidase and from 10 to 40 wt. % of fungal alpha-amylase, and thereafter hydrogenating the product of said saccharification step to form a hydrogenated starch hydrolysate containing 12 to 24 wt. % sorbitol, from 60 to 80 wt. % maltitol, and from 8 to 16 wt. % hydrogenated saccharides having a DP of 3 or more.

* * * * *

UNITED STATES PATENT AND TRADEMARK OFFICE

CERTIFICATE OF CORRECTION

PATENT NO. : 4,675,293

DATED : June 23, 1987

INVENTOR(S) : Gabriel J. Gibs

It is certified that error appears in the above-identified patent and that said Letters Patent is hereby corrected as shown below:

Column 4, claim 1, line 36, after "30," please insert --which--.

Signed and Sealed this

Third Day of November, 1987

*Attest:*

DONALD J. QUIGG

*Attesting Officer* *Commissioner of Patents and Trademarks*